United States Patent [19]

Yamada et al.

[11] Patent Number: 5,110,944

[45] Date of Patent: May 5, 1992

[54] PROCESS FOR PREPARING 5-HYDROXYHYDANTOIN

[75] Inventors: Masahiko Yamada; Satomi Takahashi, both of Kobe, Japan

[73] Assignee: Kenegafuchi Kagaku Kogyo Kabushiki Kaisha, Osaka, Japan

[21] Appl. No.: 657,800

[22] Filed: Feb. 20, 1991

[30] Foreign Application Priority Data

Feb. 23, 1990 [JP] Japan .................................. 2-43218

[51] Int. Cl.$^5$ ............................................. C07D 233/78
[52] U.S. Cl. ................................................ 548/311
[58] Field of Search ................................ 548/311, 544

[56] References Cited

PUBLICATIONS

Abblard et al., Bull. Soc. Chimique, No. 3, pp. 942–946 (1971).
Chemical Abstracts, vol. 112, No. 9, Abst. 76761 (1990).
Matsui et al., J. Org. Chem. vol. 55, No. 4, pp. 1396–1399 (2-1990).
Fieser and Fieser, Reagents for Organic Synthesis, vol. 5 p. 130 (Wiley-Interscience 1975).

*Primary Examiner*—Mary C. Lee
*Assistant Examiner*—M. S. H. Gabilan
*Attorney, Agent, or Firm*—Armstrong, Nikaido, Marmelstein, Kubovcik & Murray

[57] ABSTRACT

A process for preparing 5-hydroxyhydantoin which comprises oxidizing 4,5-dihydroxyimidazolin-2-one having formula (I):

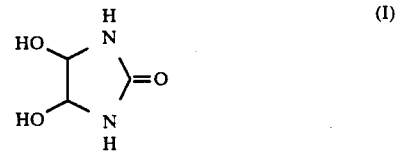

with hydrogen peroxide in an aqueous medium in the presence of a metal ion. According to the process, 5-hydroxyhydantoin is readily prepared from inexpensive starting materials.

4 Claims, No Drawings

PROCESS FOR PREPARING 5-HYDROXYHYDANTOIN

BACKGROUND OF THE INVENTION

The present invention relates to a novel process for preparing 5-hydroxyhydantoin.

5-Hydroxyhydantoin, as mentioned below, is an important compound which can be converted into 5-(p-hydroxyphenyl)hydantoin, according to the process described in Japanese Unexamined Patent Publication No. 138560/1979, which compound is a starting material for p-hydroxyphenylglycine useful for synthesis of semisynthesized penicillin or cephalosporins.

There have been known many processes for preparing 5-hydroxyhydantoin. Examples of these processes are, for instance, a method wherein alloxan is treated with alkali such as an alkali metal hydroxide or an alkaline earth metal hydroxide to give alloxanic acid, followed by decarboxylation under heating in its aqueous solution (see Berichete der Deutschen Chemischen Gesellschaft, 54B, 1802 (1921)), a method wherein parabanic acid is reduced with potassium borohydride (see Bulletin de la Societe Chimique de France, 942 (1971)), a method wherein glyoxylic acid and urea are reacted in an acidic medium (see Tetrahedron, 33, 1191 (1977)), a method wherein hydantoin is oxidized with lead tetraacetate or alkylperoxide (see Japanese Unexamined Patent Publication No. 75473/1989).

However, the methods using alloxan, parabanic acid or glyoxylic acid are not satisfiable, because the starting materials are expensive. The method wherein hydantoin is oxidized has the problem that dangerous lead tetraacetate or alkylperoxide must be used.

An object of the invention is to provide a useful process for preparing 5-hydroxyhydantoin from an inexpensive starting material.

This and other objects of the present invention will become apparent from the description hereinafter.

SUMMARY OF THE INVENTION

It has now been found that a novel process for preparing 5-hydroxyhydantoin wherein 4,5-dihydroxyimidazolin-2-one, which can be synthesized from inexpensive glyoxal, is used as a starting material.

The present invention provides a process for preparing 5-hydroxyhydantoin which comprises oxidizing 4,5-dihydroxyimidazolin-2-one having formula (I):

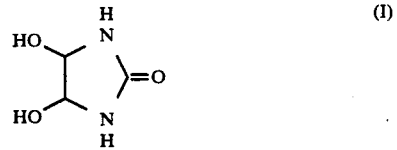

with hydrogen peroxide in an aqueous medium in the presence of a metal ion.

DETAILED DESCRIPTION 4,5-Dihydroxyimidazolin-2-one used as a starting material in the present invention is a compound represented by the above-mentioned.

This compound can be synthesized very easily in a high yield by the reaction of inexpensive glyoxal and urea, for example, as described in Berichete der Deutschen Chemischen Gesellschaft, 63B, 2063 (1930).

In the present invention, it is not always necessary to use a purified 4,5-dihydroxyimidazolin-2-one. A crude product synthesized by the above-mentioned process may be used as it is.

The metal ion is used as a catalyst for the oxidative reaction. Examples of the metal ion include divalent iron ion and univalent copper ion. From the viewpoint of practical use, divalent iron ion is preferable. For supplying these metal ions, for instance, iron (II) salt such as iron (II) sulfate or iron (II) chloride, or copper (I) salt such as copper (I) sulfate or copper (I) chloride is used. The preferable amount of the metal ion to be used is not necessarily limited, since it is variable depending upon other reaction conditions. However, from the viewpoint of increasing the rate of conversion into 5-hydroxyhydantoin, a preferable amount of the metal ion is not less than about 0.01 mole per 1 mole of 4,5-dihydroxyimidazolin-2-one, which is the substrate of the reaction. There is no strict upper limit for the amount. However, in order to avoid the precipitation of excess iron ion, the upper limit is preferably about five times by mole as much as the amount of 4,5-dihydroxyimidazolin-2-one.

As the hydrogen peroxide used as an oxidizing agent, a 30 to 60% (by weight, hereinafter the same) aqueous solution of hydrogen peroxide which is commercially available can be used as it is or in an appropriately diluted state. The concentration of hydrogen peroxide is not particularly limited and usually from 10 to 40%. The amount of hydrogen peroxide to be used is preferably from 0.8 to 2 times by mole as much as that of 4,5-dihydroxyimidazolin-2-one.

In the present invention, an aqueous medium is used as a reaction medium from the viewpoint of solubility of 4,5-dihydroxyimidazolin-2-one as the starting material. Examples of the aqueous medium include water and mixed solvent of water and alcohol. Water is preferably used due to its most practical use.

The amount of aqueous medium to be used is not particularly limited and usually about from 1 to 50 times by weight as much as that of 4,5-dihydroxyimidazolin-2-one.

In the present invention, 5-hydroxyhydantoin is prepared by oxidizing 4,5-dihydroxyimidazolin-2-one with hydrogen peroxide in an aqueous medium in the presence of a metal ion. Concretely, for example, the reaction can be conducted by adding a solution of hydrogen peroxide to an aqueous solution of 4,5-dihydroxyimidazolin-2-one by means of dropping, etc.. With respect to the manner of addition of the metal ion, the whole of the necessary amount of the matal ion may be added to the solution containing 4,5-dihydroxyimidazolin-2-one before the beginning of addition of hydrogen peroxide, or the necessary amount of the metal ion may be added to the solution in a manner such as dropping in the course of the reaction, separately from the addition of hydrogen peroxide.

For the purpose of obtaining 5-hydroxyhydantoin in a high selectivity, the reaction is preferably carried out with preventing the reaction mixture from coming into contact with a gas phase containing molecular oxygen such as air. Accordingly, it is preferable to remove the dissolved oxygen from the solution containing 4,5-dihydroxyimidazolin-2-one and/or the hydrogen peroxide solution prior to the reaction by passing nitrogen gas through them and to carry out the reaction while passing nitrogen gas through the reaction vessel. Further, in order to prevent the metal ion from oxidation with light, it is preferable to shield the reaction system from light.

The reaction temperature is generally from about 0° to about 50° C., which temperature is so-called ordinary temperature. Preferably the oxidative reaction is carried out in the range of from about 0° to about 15° C. When the reaction temperature is more than 50° C., the yield of 5-hydroxyhydantoin lowers.

The reaction time is not particularly limited and generally from about 0.5 to about 10 hours.

The pH in the oxdative reaction, from the viewpoint of suppressing side reactions, is from 1 to 10, preferably from about of 2 to about 8. Since the pH tends to lower with the progress of reaction, the pH may be kept constant by using a pH-stat.

After removing solid parabanic acid as a by-product from the thus obtained reaction product by filtration, etc., 5-hydroxyhydantoin as the desired compound may be isolated and purified by column chromatography, etc.. Thus, 5-hydroxyhydantoin can be prepared in a high yield.

As explained above, according to the process of present invention wherein 4,5-dihydroxyimidazolin-2-one is oxidized with hydrogen peroxide in the presence of metal ion, 5-hydroxyhydantoin, which can be converted into 5-(p-hydroxyphenyl)hydantoin, can be prepared readily and inexpensively.

The process of the present invention is more specifically described and explained by means of the following Examples in which all per cents and parts are by weight unless otherwise noted. It is to be understood that the present invention is not limited to the Examples, and various changes and modifications may be made in the invention without departing from the spirit and scope thereof.

REFERENCE EXAMPLE 1

Preparation of 4,5-dihydroxyimidazolin-2-one

A 100 ml-flask was charged with 10.0 ml of a 40% aqueous solution of glyoxal (0.086 mole as the amount of glyoxal) and 7.7 g (0.129 mole) of urea. The mixture was stirred in a nitrogen atmosphere with shading light at 30° C. for 90 minutes. After the reaction, the reaction product was analyzed by high performance liquid chromatography using a 0.05% aqueous solution of phosphoric acid as a mobile phase and Shodex KC-811 column as a separating column. The analysis indicated the formation of 9.1 g (yield: 90%) of 4,5-dihydroxyimidazolin-2-one.

The particulars of the high performance liquid chromatography were as follows.
Apparatus: High performance chromatograph TRIRO-TAR, made by Japan Spectroscopic Co., LTD
Column: Shodex KC-811 column, made by Showa Denko Kabushiki Kaisha
Developping solvent: 0.05% aqueous solution of phosphoric acid
Flow rate: 0.08 ml/min.
Detection: 210 nm, with UV detector The retention time of the 4,5-dihydroxyimidazolin-2-one imidazolin-2-one was 11.3 minutes under these conditions. The Rf value obtained by thin layer chromatography with silica gel was 0.27 (BuOH:CH$_3$CO$_2$H:H$_2$O=4:1:1 by volume). These values completely coincided with those of a standard sample synthesized by the known method described in Berichete der Deutschen Chemischen Gesellschaft, 63B, 2063 (1930).

The standard sample was identified by $^1$H-NMR. The results were as follows.
$^1$H-NMR (90 MHz, d$_6$-DMSO)δppm: 6.00 (1H, s. br), 4.80 (1H, d (J=5.1 Hz)), 3.57 (1H, d (J=5.1 Hz)), 2.37 (3H, s)

EXAMPLE 1

Preparation of 5-hydroxyhydantoin

Twenty ml of water and 139 mg (0.5 millimole) of iron (II) sulfate heptahydrate were added to 2.2 g of an aqueous solution containing 0.71 g (6 millimole) of 4,5-dihydroxyimidazolin-2-one which was obtained by reacting an aqueous solution of glyoxal and urea in the same way as in Reference Example 1. Then, thereto was added dropwise 1 ml of a 30% aqueous solution of hydrogen peroxide over 1 hour at room temperature, and the reaction was further continued for 1 hour at room temperature. The obtained reaction product was analyzed by high performance chromatography using a 0.05% aqueous solution of phosphoric acid containing 8% of methanol as a mobile phase and Shodex KC-811 column as a separating column. The analysis indicated the formation of 5-hydroxyhydantoin in a yield of 40%.

The particulars of the high performance chromatography were as follows.
Apparatus: High performance chromatograph TRIRO-TAR, made by Japan Spectroscopic Co., LTD
Column: Shodex KC-811 column, made by Showa Denko Kabushiki Kaisha
Developing solvent: 0.05% aqueous solution of phosphoric acid containing 8% of methanol
Flow rate: 0.7 ml/min
Detection: 210 nm, with UV detector The retention time of the 5-hydroxyhydantoin was 12.5 minutes under these conditions. The Rf value obtained by thin layer chromatography with silica gel was 0.64 (BuOH:CH$_3$CO$_2$H:H$_2$O=4:1:1, by volume). These values completely coincided with those of a standard sample synthesized by the known method described in Bulletin de la Societe Chimique de France, 942 (1971).

The standard sample was identified by $^1$H-NMR. The results were as follows.
$^1$H-NMR (90 MHz, d$_6$-DMSO)δppm: 10.5 (1H, s), 8.25 (1H, br.), 7.00 (1H, br.), 5.11 (1H, d), 10.5 (1H, s), 8.25 (1H, br.), 7.00 (1H, br.), 5.11 (1H, d)

EXAMPLE 2

Twentyfour ml of water was added to 20.2 g of an aqueous solution containing 9.1 g (77 millimole) of 4,5-dihydroxyimidazolin-2-one which was obtained by reacting an aqueous solution of glyoxal and urea in the same way as in Reference Example 1. After the obtained mixture was adjusted to pH 3.0 by adding a concentrated hydrochloric acid dropwise, it was stirred in a nitrogen atmosphere for 30 minutes. While adjusting this reaction system to pH 3.0 with a pH-stat, thereto were added dropwise 10 ml of a 27% aqueous solution of hydrogen peroxide through which nitrogen gas had been passed and 10 ml of an aqueous solution containing 600 mg of iron (II) sulfate heptahydrate through which nitrogen gas had been passed, in the same rate through the respective dropping holes over 8 hours with ice-cooling. The reaction was further continued for 1 hour with ice-cooling. All operations mentioned above were carried out shaded from light.

The obtained reaction product was analyzed by high performance liquid chromatography. The analysis indicated the formation of 5.38 g (yield: 63%) of 5-hydroxyhydantoin.

REFERENCE EXAMPLE 2

Preparation of 5-(4-hydroxyphenyl)hydantoin

Sixty ml of the reaction solution obtained in Example 2 containing 5.38 g of 5-hydroxyhydantoin was filtrated to remove the solid parabanic acid which was produced as a by-product in the reaction solution. Then the filtrate was added dropwise to a mixture of 4.5 g of phenol and 20 ml of a concentrated hydrochloric acid at 70° C. over 10 hours.

The formed white precipitate was taken by filtration, washed with water and dried to give 6.0 g of the desired 5-(4-hydroxyphenyl)hydantoin (63% yield from 5-hydroxyhydantoin).

The identification of the product was carried out by high performance liquid chromatography and thin layer chromatography with silica gel.

The particulars of the high performance liquid chromatography were as follows.

Apparatus: High performance chromatograph TRIRO-TAR, made by Japan Spectroscopic Co., LTD
Column: YMC Packed Column A-303 S-5 120A ODS, made by YMC Kabushiki Kaisha
Developing solvent: phosphate buffer solution (pH 2.5) containing 13% of acetonitrile
Flow rate: 0.7 ml/min
Detection: 210 nm, with UV detector The retention time of the 5-(4-hydroxyphenyl)hydantoin was 7.1 minutes under these conditions. The Rf value obtained by thin layer chromatography with silica gel was 0.83 ($BuOH:CH_3CO_2H:H_2O=4:1:1$ by volume). These values completely coincided with those of a standard sample synthesized by the known method described in Japanese Examined Patent Publication No. 22474/1980 (Japanese Unexamined Patent Publication No. 138560/1979).

In addition to the ingredients used in the Examples, other ingredients can be used in the Examples as set forth in the specification to obtain substantially the same results.

What we claim is:

1. A process for preparing 5-hydroxyhydantoin which comprises oxidizing 4,5-dihydroxyimidazolin-2-one with hydrogen peroxide in an aqueous medium in the presence of a metal ion selected from the group consisting of divalent iron ion and monovalent copper ion.

2. The process of claim 1, wherein the metal ion is divalent iron ion.

3. The process of claim 1, wherein the 4,5-dihydroxyimidazolin-2-one is prepared in an aqueous solution by the reaction of glyoxal with urea, and hydrogen peroxide and divalent iron ion or monovalent copper ion are added to the aqueous solution.

4. The process of claim 1, wherein the aqueous medium is free of molecular oxygen and is shielded from light.

* * * * *